(12) United States Patent
Mizutaki et al.

(10) Patent No.: US 10,407,584 B2
(45) Date of Patent: Sep. 10, 2019

(54) WATER-BASED INK COMPOSITION AND METHOD OF DISCHARGING LIQUID DROPLET

(71) Applicant: Seiko Epson Corporation, Tokyo (JP)

(72) Inventors: Yusuke Mizutaki, Shiojiri (JP); Tomohito Nakano, Shiojiri (JP); Wataru Ito, Chino (JP); Atsushi Muto, Shiojiri (JP); Hiroshige Owaki, Okaya (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/607,822

(22) Filed: May 30, 2017

(65) Prior Publication Data

US 2017/0369723 A1 Dec. 28, 2017

(30) Foreign Application Priority Data

Jun. 28, 2016 (JP) ................. 2016-127759

(51) Int. Cl.
| | |
|---|---|
| *B41J 2/04* | (2006.01) |
| *C09D 11/322* | (2014.01) |
| *B41J 2/135* | (2006.01) |
| *C07D 221/18* | (2006.01) |
| *C09D 11/326* | (2014.01) |
| *C09D 11/38* | (2014.01) |

(52) U.S. Cl.
CPC .............. *C09D 11/322* (2013.01); *B41J 2/04* (2013.01); *B41J 2/135* (2013.01); *C07D 221/18* (2013.01); *C09D 11/326* (2013.01); *C09D 11/38* (2013.01); *B41J 2202/01* (2013.01)

(58) Field of Classification Search
None
See application file for complete search history.

(56) References Cited

U.S. PATENT DOCUMENTS

| | | | |
|---|---|---|---|
| 2008/0273045 A1* | 11/2008 | Morohoshi ......... | B41M 5/5218 346/135.1 |
| 2010/0087595 A1 | 4/2010 | Koganehira et al. | |
| 2011/0122197 A1* | 5/2011 | Shin ..................... | B41J 2/14233 347/47 |
| 2011/0242196 A1* | 10/2011 | Okada ................... | B41J 2/2146 347/20 |
| 2012/0232203 A1 | 9/2012 | Tomura et al. | |
| 2013/0224451 A1* | 8/2013 | Shiono ................... | C09D 11/38 428/207 |

(Continued)

FOREIGN PATENT DOCUMENTS

| | | |
|---|---|---|
| EP | 0712912 A2 | 5/1996 |
| EP | 1247845 A1 | 10/2002 |

(Continued)

OTHER PUBLICATIONS

Extended European Search Report for Patent Application No. EP 17176707.2 dated Sep. 5, 2017 (6 pages).

*Primary Examiner* — Erica S Lin
(74) *Attorney, Agent, or Firm* — Harness, Dickey & Pierce, P.L.C.

(57) ABSTRACT

A water-based ink includes a pigment, and water, in which a viscosity at 20° C. is in a range of 2 mPa·s to 7 mPa·s, and a yield value at 20° C. is less than 0.2 mPa, and the yield value at 20° C. when evaporating 25% of the water is less than 0.8 mPa.

14 Claims, 5 Drawing Sheets

(56) References Cited

U.S. PATENT DOCUMENTS

2014/0285582 A1    9/2014  Watanabe et al.

FOREIGN PATENT DOCUMENTS

| | | |
|---|---|---|
| JP | 08-325491 A | 12/1996 |
| JP | 2005-002186 A | 1/2005 |
| JP | 2006-176759 A | 7/2006 |
| JP | 2012-184365 A | 9/2012 |
| JP | 2014037495 A * | 2/2014 |
| JP | 2014-184606 A | 10/2014 |

* cited by examiner

WATER-BASED INK COMPOSITION AND METHOD OF DISCHARGING LIQUID DROPLET

BACKGROUND

1. Technical Field

The present invention relates to a water-based ink composition and a method of discharging a liquid droplet.

2. Related Art

An ink jet recording apparatus that is an example of a liquid ejecting apparatus includes a discharging head having a nozzle hole for discharging an ink, a driving unit (for example, a piezoelectric vibrator or a heater element) for discharging the ink from the nozzle hole, and a control unit for controlling the driving unit according to data. For example, supply of the ink to the nozzle hole is performed by an ink cartridge or an ink supply chamber that receives the ink from an ink cartridge, and an ink supply passage extending from the ink supply chamber to the nozzle hole. The ink cartridge is usually exchangeable.

In recent years, a new discharging head which achieves a size reduction and space saving and can realize a high speed and high quality image by setting an arrangement density of nozzle holes higher than an arrangement of the related art is developed (for example, refer to JP-A-2014-184606).

The nozzle hole of the new discharging head is formed by dry etching a silicon substrate for realizing a high arrangement density and multiple nozzles. It is known that a side wall of the nozzle hole formed such that manner has a waveform shape as seen on a scallop shell surface which is called scallop.

The present inventors of the present application have found that in a case where an ink jet recording apparatus including the above-described new discharging head is placed under a high temperature environment, there is a new problem that alignment deterioration easily occurs when a water-based ink containing a pigment is discharged. In a case where such a side wall of the nozzle hole has a scallop structure, a water-based ink in the passage cannot follow a movement of a meniscus, and the divided water-based ink is adhered on an uneven structure of the side wall of the passage. The alignment deterioration occurs due to evaporation or thickening of the adhered water-based ink. Accordingly, it is considered that continuous printing stability is deteriorated.

On the other hand, an ink composition in which a thixotropy index is adjusted and which is effective for clogging recoverability or bleeding is disclosed (for example, refer to JP-A-2012-184365). In addition, an ink composition to which a thixotropy agent is added in order to suppress sedimentation of a pigment is disclosed (for example, refer to JP-A-8-325491).

However, even when these ink compositions are used, a sufficient effect cannot be exerted with respect to the object of the continuous stability due to the alignment deterioration occurring in the above-described new discharging head.

SUMMARY

An advantage of some aspects of the invention is to provide a water-based ink composition excellent in the continuous printing stability even under a high temperature environment, in particular, a water-based ink composition excellent in the continuous printing stability in a case where an ink jet recording apparatus including the above-described new discharging head is placed under the high temperature environment.

Furthermore, an advantage of some aspects of the invention is to provide a water-based ink composition which is excellent in the continuous printing stability under the high temperature environment and in which sedimentation of a pigment hardly occurs.

The invention can be realized in the following aspects or application examples.

APPLICATION EXAMPLE 1

According to a water-based ink composition related to an aspect of the invention, there is provided a water-based ink composition including a pigment and water, in which a viscosity at 20° C. is in a range of 2 mPa·s to 7 mPa·s, and a yield value at 20° C. is less than 0.2 mPa, and the yield value at 20° C. when evaporating 25% of the water is less than 0.8 mPa.

According to the water-based ink composition of Application Example 1, since the viscosity in a low shearing region and the viscosity in a high shearing region can be reduced, the continuous printing stability is excellent even under the high temperature environment.

APPLICATION EXAMPLE 2

In the water-based ink composition according to Application Example 1, an average particle diameter of the pigment can be 80 nm or more and less than 160 nm.

According to the water-based ink composition of Application Example 2, it is excellent in the continuous printing stability even under the high temperature environment, and since the sedimentation of the pigment hardly occurs during storage of the ink, it is also excellent in storage stability.

APPLICATION EXAMPLE 3

In the water-based ink composition according to Application Example 1 or Application Example 2, the pigment can be a pigment having a quinacridone skeleton.

According to the water-based ink composition of Application Example 3, even when the pigment is the pigment having quinacridone skeleton with strong cohesion force compared to the other pigments, it is excellent in the continuous printing stability in the high temperature environment.

APPLICATION EXAMPLE 4

In the water-based ink composition according to Application Example 3, the pigment having the quinacridone skeleton can be at least one selected from the group consisting of C.I. Pigment Red 122, C.I. Pigment Red 202, and C.I. Pigment Violet 19.

According to the water-based ink composition of Application Example 4, even when the pigment is C.I. Pigment Red 122, C.I. Pigment Red 202, or C.I. Pigment Violet 19 with the strong cohesion force compared to the other pigments, it is excellent in the continuous printing stability in the high temperature environment.

APPLICATION EXAMPLE 5

The water-based ink composition according to any one of Application Example 1 to Application Example 4, the water-based ink composition can be for use in an ink jet recording apparatus including a discharging head having a nozzle substrate in which a discharging port for discharging a liquid is formed and repeated uneven shapes formed on a side wall surface in the vicinity of the discharging port.

In a case where the above-described ink jet recording apparatus is placed under the high temperature environment, the alignment deterioration easily occurs when the water-based ink containing the pigment is discharged. However, by using the water-based ink composition of any one of Application Example 1 to Application Example 4, the continuous printing stability is excellent even under the high temperature environment.

APPLICATION EXAMPLE 6

In the water-based ink composition according to Application Example 5, when a depth of a concave portion formed on the side wall surface in the vicinity of the discharging port is defined as a and a distance between adjacent convex portions is defined as b, a relation of b/a≥4 can be satisfied.

Since the uneven shape of the side wall surface of a second liquid passage has the above-described shape, stagnation of a step portion disappears, and the ink easily follows the meniscus. Accordingly, since the ink is not remained in the step portion, the continuous printing stability under the high temperature environment is further improved.

APPLICATION EXAMPLE 7

According to a method of discharging a liquid droplet related to another aspect of the invention, there is provided a method of discharging a liquid droplet including discharging the water-based ink composition according to any one of Application Example 1 to Application Example 4 onto a recording medium by a discharging head.

According to the method of discharging a liquid droplet of Application Example 7, since the viscosity in a low shearing region and the viscosity in a high shearing region can be reduced by using the above-described water-based ink composition, the continuous printing stability is excellent even under the high temperature environment.

APPLICATION EXAMPLE 8

According to the method of discharging a liquid droplet of Application Example 7, the discharging head includes a nozzle substrate in which a discharging port for discharging a liquid is formed, and can have repeated uneven shapes formed on a side wall surface in the vicinity of the discharging port.

In a case where the above-described ink jet recording apparatus including the discharging head is placed under the high temperature environment, the alignment deterioration easily occurs when the water-based ink containing the pigment is discharged. However, by using the above-described water-based ink composition, the continuous printing stability is excellent even under the high temperature environment.

APPLICATION EXAMPLE 9

In the method of discharging a liquid droplet according to Application Example 8, when a depth of a concave portion formed on the side wall surface in the vicinity of the discharging port is defined as a and a distance between adjacent convex portions is defined as b, a relation of b/a≥4 can be satisfied.

Since the uneven shape of the side wall surface of a second liquid passage has the above-described shape, stagnation of a step portion disappears, and the ink easily follows the meniscus. Accordingly, since the ink is not remained in the step portion, the continuous printing stability under the high temperature environment is further improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

Several embodiments of the invention are described below. The following embodiments explain an example of the invention. The invention is not limited to the following embodiments. The invention includes various modifications that can be practiced without departing from the scope of the invention. Note that, all of the configurations described below should not necessarily be taken as essential configurations of the invention.

In the specification, the terms of "under a high temperature environment" means under an environment in an operating temperature in the summer or the like, and specifically means under the environment of about 30° C. to 50° C.

In the specification, the terms of a "yield value" represents a minimum stress value required to flow the ink, and represents a Casso yield value calculated by Casson-Plot.

1. Water-Based Ink Composition

A water-based ink composition according to the present embodiment includes a pigment and water, in which a viscosity at 20° C. is in a range of 2 mPa·s to 7 mPa·s, and a yield value at 20° C. is less than 0.2 mPa, and the yield value at 20° C. when evaporating 25% of the water is less than 0.8 mPa. In the water-based ink composition according to the present embodiment, by lowering the viscosity in a low shearing region and the viscosity in a high shearing region, the continuous printing stability is excellent even under the high temperature environment.

In the water-based ink composition according to the present embodiment, for example, by adjusting the types, the average particle diameter and the mixing amount of the pigment, the viscosity at 20° C. is set to 2 mPa·s to 7 mPa·s, and preferably to 3 mPa·s to 5 mPa·s. Accordingly, it is possible to obtain the water-based ink composition with excellent in discharge stability (stability of discharging amount, flight characteristic of a liquid droplet, or the like), discharging responsiveness (response speed, high-frequency responsiveness (frequency characteristic), or the like), or the like. The viscosity of the water-based ink composition at 20° C. can be measured by the Rheometer MCR301 (manufactured by Anton Paar).

In the water-based ink composition according to the present embodiment, for example, by adjusting the types, the average particle diameter and the mixing amount of the pigment, the yield value at 20° C. is set to less than 0.2 mPa and the yield value at 20° C. when evaporating 25% of the water is set to less than 0.8 mPa. The yield value at 20° C. is required to be less than 0.2 mPa, preferably 0 mPa. The yield value at 20° C. when evaporating 25% of the water is required to be less than 0.8 mPa, preferably 0.6 mPa or less, more preferably 0.2 mPa or less, and particularly preferably 0 mPa. By lowering the viscosity in a low shearing region and the viscosity in a high shearing region, the continuous printing stability is excellent even under the high temperature environment. The yield value can be obtained by performing rheology measurement at a shearing rate of 0.01 to 1 s$^{-1}$ using the Rheometer MCR301 (manufactured by Anton Paar) at 20° C. and analyzing the obtained data by the Casson-Plot.

The "yield value at 20° C. when evaporating 25% of water" can be restated as the yield value at 20° C. when the water is evaporated until a residual amount of the water reaches 75% with respect to the total mass (100%) of the water contained in the ink.

Hereinafter, a component contained in the water-based ink composition according to the present embodiment will be described.

1.1 Pigment

The water-based ink composition according to the present embodiment contains a pigment. By using the pigment, it is possible to improve light resistances and color developing properties of the ink. As the pigment, both an inorganic pigment and an organic pigment can be used.

As the inorganic pigment, carbons such as furnace black, lamp black (C.I. Pigment Black 6), acetylene black, channel black, or carbon black (C.I. Pigment Black 7), iron oxide, and titanium oxide can be used.

Examples of the organic pigment include an azo pigment such as an insoluble azo pigment, a condensed azo pigment, azo lake, or a chelating azo pigment, a polycyclic pigment such as a phthalocyanine pigment, a perylene and perinone pigment, an anthraquinone pigment, a quinacridone pigment, a dioxane pigment, a thioindigo pigment, an isoindolinone pigment, or a quinophthalone pigment, a dye chelate (for example, a basic dye-type chelate, an acidic dye-type chelate, or the like), a dye lake (a basic dye-type lake, an acidic dye-type lake, or the like), a nitro pigment, a nitroso pigment, aniline black (C.I. Pigment Black 1), and a daylight fluorescent pigment.

Specific examples of the carbon black to be used as the black ink includes No. 2300, No. 900, MCF88, No. 33, No. 40, No. 45, No. 52, MA7, MA8, MA100, No. 2200B, or the like (all manufactured by Mitsubishi Chemical Corporation), Raven 5750, Raven 5250, Raven 5000, Raven 3500, Raven 1255, Raven 700, or the like (all manufactured by Columbia Carbon Inc.), Regal 400R, Regal 330R, Regal 660R, Mogul L, Monarch 700, Monarch 800, Monarch 880, Monarch 900, Monarch 1000, Monarch 1100, Monarch 1300, Monarch 1400, or the like (manufactured by Cabot Corporation), Color Black FW1, Color Black FW2, Color Black FW2V, Color Black FW18, Color Black FW200, Color Black S150, Color Black S160, Color Black S170, Printex 35, Printex U, Printex V, Printex 140U, Special Black 6, Special Black 5, Special Black 4A, and Special Black 4 (all manufactured by Degussa).

Examples of the pigment to be used in a white ink include C.I. Pigment White 6, 18, and 21.

Examples of the pigment used in a yellow ink include C.I. Pigment Yellow 1, 2, 3, 4, 5, 6, 7, 10, 11, 12, 13, 14, 16, 17, 24, 34, 35, 37, 53, 55, 65, 73, 74, 75, 81, 83, 93, 94, 95, 97, 98, 99, 108, 109, 110, 113, 114, 117, 120, 124, 128, 129, 133, 138, 139, 147, 151, 153, 154, 167, 172, and 180.

Examples of the pigment used in a magenta ink include C.I. Pigment Red 1, 2, 3, 4, 5, 6, 7, 8, 9, 10, 11, 12, 14, 15, 16, 17, 18, 19, 21, 22, 23, 30, 31, 32, 37, 38, 40, 41, 42, 48 (Ca), 48 (Mn), 57 (Ca), 57:1, 88, 112, 114, 122, 123, 144, 146, 149, 150, 166, 168, 170, 171, 175, 176, 177, 178, 179, 184, 185, 187, 202, 209, 219, 224, 242, and 245, or C.I. Pigment Violet 19, 23, 32, 33, 36, 38, 43, and 50.

Examples of the pigment used in a cyan ink include C.I. Pigment Blue 1, 2, 3, 15, 15:1, 15:2, 15:3, 15:34, 15:4, 16, 18, 22, 25, 60, 65, and 66, and C.I. Vat Blue 4 and 60.

In addition, examples of the pigment other than magenta, cyan, and yellow include C.I. Pigment Green 7, 10, and 36, C.I. Pigment Brown 3, 5, 25, and 26, and C.I. Pigment Orange 1, 2, 5, 7, 13, 14, 15, 16, 24, 34, 36, 38, 40, 43, and 63.

The pigment may be used alone or in combination of two or more of pigments.

Among the pigments, since the pigment having quinacridone skeleton has strong hydrophobic and strong cohesion force compared to the other pigments, the pigment tends to be difficult to disperse in the ink. In addition, since the cohesion force is high even if the pigment can be dispersed in the ink, there is the characteristic that is easy to have higher yield value. Therefore, the water-based ink composition containing the pigment having the quinacridone skeleton tends to cause alignment deterioration under the high temperature environment. However, even in a case where the water-based ink composition according to the present embodiment contains the pigment having quinacridone skeleton, for example, for example, by lowering the viscosity of the low shearing region and the viscosity in the high shearing region by adjusting the types, the average particle diameter and the mixing amount of the pigment, the continuous discharging stability under the high temperature environment is improved.

Examples of the pigment having the quinacridone skeleton include C.I. Pigment Violet 19, C.I. Pigment Red 122, 202, and 209, C.I. Pigment Orange 48 and 49, and the like. Among these, in a case where the pigment is at least one selected from the group consisting of C.I. Pigment Red 122, C.I. Pigment Red 202, and C.I. Pigment Violet 19, the effect of the invention of the present application can further be easily obtained. In a case where the pigment is a solid solution of C.I. Pigment Red 202 and C.I. Pigment Violet 19, the effect of the invention of the present application can be particularly easily obtained.

In a case of using the pigment, the average particle diameter is preferably 80 nm or more and less than 160 nm, and more preferably 100 nm to 155 nm.

If the average particle diameter of the pigment is within the above-described range, the continuous printing stability is excellent even under the high temperature environment, since the sedimentation of the pigment hardly occurs during storage of the ink, it is also excellent in storage stability. Here, the terms of the "average particle diameter" in the specification means a particle diameter D50 at 50% cumulation in a case where the total volume of the group of the particles is defined as 100%. For example, the average particle diameter can be obtained by measuring with a dynamic light scattering type nano-track particle size analyzer (manufactured by Nikkiso Co., Ltd., Type "Nanotrac 150"), for example.

The content of the pigment is preferably 0.1% to 30% by mass, more preferably 0.5% to 15% by mass, and particularly preferably 1% to 10% by mass, with respect to the total mass (100% by mass) of the water-based ink composition. When the content of the pigment is within the range, the dispersion stability is excellent, the viscosity of the water-based ink composition tends to be a proper degree, and the image such as characters or figures excellent in color developing properties can be recorded.

These pigments are preferably blended in the water-based ink composition as a pigment dispersion liquid dispersed in an aqueous medium with a dispersant.

As the dispersant, a styrene-acylic acid copolymer or the like is exemplified, and the dispersant having the weight average molecular weight of about 10,000 to 150,000 is preferable from the viewpoint of stably dispersing the pigment.

1.2 Water

Water contained in the water-based ink composition according to the present embodiment is a main solvent, and it is preferable to use pure water such as ion exchanged water, ultrafiltered water, reverse osmosis water, distilled water or ultrapure water. In particular, it is preferable to use water which is sterilized by ultraviolet irradiation or addition of hydrogen peroxide, from the viewpoint of preventing the generation of fungi and bacteria and enabling preservation the water-based ink composition for a long period of time.

The content of the water in the water-based ink composition according to the present embodiment is preferably 30% by mass or more, more preferably 50% to 95% by mass, and particularly preferably 60% to 90% by mass, with respect to the total mass (100% by mass) of the water-based ink composition. Here, the content of the water is not limited to the amount of water added, and in a case of adding the other additives, the content of the water is that the water in the additives is included.

In the specification, the terms of "water-based ink composition" means an ink composition containing 30% by mass or more of the water, with respect to the total mass (100% by mass) of the ink composition.

1.3 Water-Soluble Organic Solvent

A water-soluble organic solvent may be added in the water-based ink composition according to the present embodiment. By adding the water-soluble organic solvent, it is possible to prevent drying in the vicinity of the nozzle of the ink and effectively prevent clogging of the discharging head. Examples of the water-soluble organic solvent include monohydric alcohols, polyhydric alcohols, and derivative thereof.

In particular, examples of the monohydric alcohol include monohydric alcohols having 1 to 4 carbon atoms, for example, methanol, ethanol, n-propanol, i-propanol, n-butanol, and the like.

As the polyhydric alcohols and derivatives thereof, dihydric to pentahydric alcohols having 2 to 6 carbon atoms, and complete or partial ethers thereof with lower alcohols having 1 to 4 carbon atoms can be used. Here, the polyhydric alcohol derivative is an alcohol derivative in which at least one hydroxyl group is etherified, and does not mean a polyhydric alcohol without etherified hydroxyl group itself.

Specific examples of these polyhydric alcohols and derivatives thereof include polyhydric alcohols such as glycerin, 1,2-propanediol, 1,3-propanediol, 1,2-pentanediol, 1,2-hexanediol, 1,3-hexanediol, 1,2-heptanediol, 1,3-heptanediol, 1,2-octanediol, 1,3-octanediol, 1,2,6-hexanetriol, trimethylolpropane, ethylene glycol, diethylene glycol, triethylene glycol, tetraethylene glycol, pentaethylene glycol, polyethylene glycol having a number average molecular weight of 2,000 or less, tripropylene glycol, isobutylene glycol, 2-butene-1,4-diol, 2-ethyl-1,3-hexanediol, 2-methyl-2,4-pentanediol, mesoerythritol, or pentaerythritol; mono-, di- or triethylene glycol, mono- or di-alkyl ether, mono-, di- or tripropylene glycol, mono- or di-alkyl ether, or glycerin. Among these, triethylene glycol, 1,2-hexanediol, triethylene glycol monobutyl ether, diethylene glycol monobutyl ether, diethylene glycol monopropyl ether, diethylene glycol monopentyl ether, diethylene glycol-2-ethylhexyl ether, propylene glycol monobutyl ether, glycerin, and the like are preferable.

The content of the water-soluble organic solvent is preferably 5% to 30% by mass and more preferably 10% to 25% by mass, with respect to the total mass (100% by mass) of the water-based ink composition.

1.4 Surfactant

The water-based ink composition according to the present embodiment may contain a surfactant. As the surfactant, any of a nonionic surfactant, an anionic surfactant, a cationic surfactant, and an amphoteric surfactant can be used, and these surfactants may be used in combination.

As the nonionic surfactant, the surfactant is preferably at least one selected from the group consisting of an acetylene glycol surfactant, an acetylene alcohol surfactant, a fluorine surfactant, and a silicone surfactant. These nonionic surfactants are excellent in ability to properly maintain surface tension and interfacial tension of water-based ink composition. Accordingly, since it is possible to properly maintain the surface tension and the interfacial tension between printer members contacting with the ink of the head nozzle surface or the like, when the effect is applied to the ink jet recording system, the discharging stability can be improved.

The above-described acetylene glycol-based surfactant and acetylene alcohol-based surfactant are not limited to the following materials. As the acetylene glycol-based surfactant and acetylene alcohol-based surfactant, one or more selected surfactant selected from an alkylene oxide adduct of 2,4,7,9-tetramethyl-5-decyne-4,7-diol and 2,4,7,9-tetramethyl-5-decyne-4,7-diol, and an alkylene oxide adduct of 2,4-dimethyl-5-decyn-4-ol, and 2,4-dimethyl-5-decyn-4-ol, 3,6-dimethyl-4-octyne-3,6-diol, 3,5-1-hexyn-3-ol, 2,4-dimethyl-5-hexyn-3-ol.

In addition, as the acetylene glycol surfactant and the acetylene alcohol surfactant, commercially available products can also be used, and examples thereof include Surfynol 104, 104E, 104H, 104A, 104BC, 104DPM, 104PA, 104PG-50, 104S, 420, 440, 465, 485, SE, SE-F, 504, 61, DF37, CT111, CT121, CT131, CT136, TG, and GA (all of them are trade names, manufactured by Air Products and Chemicals. Inc.), Olfine B, Y, P, A, STG, SPC, E1004, E1010, PD-001, PD-002W, PD-003, PD-004, EXP. 4001, EXP. 4036, EXP. 4051, AF-103, AF-104, AK-02, SK-14, and AE-3 (all of them are trade names, manufactured by Nissin Chemical Co., Ltd.), Acetyleno E00, E00P, E40, and E100 (all of them are trade names, manufactured by Kawaken Fine Chemicals Co., Ltd.), or the like.

As the fluorine-containing surfactant, a commercially available surfactant may be used, and examples thereof include MEGAFACE F-479 (manufactured by DIC Corporation) and BYK-340 (manufactured by BYK Japan K.K.).

As the silicone surfactants, a commercially available surfactant may be used, and examples thereof include Silface SAG503A, Olfine PD-501, Olfine PD-502, and Olfine PD-570 (all manufactured by Nissin Chemical Industry Co., Ltd.), BYK-347 and BYK-348 (all manufactured by BYK-Chemie), or the like.

Furthermore, as the nonionic surfactant include polyoxyethylene alkyl ether, polyoxyethylene alkyl phenyl ether, alkyl glucoside, polyoxyalkylene glycol alkyl ether, polyoxyalkylene glycol, polyoxyalkylene glycol alkyl phenyl ether, sucrose Fatty acid esters, polyoxyethylene fatty acid esters, polyoxyethylene sorbitan fatty acid esters, sorbitan fatty acid esters, polyoxyalkylene acetylene glycols, polyoxyalkylene glycol alkyl amines, polyoxyethylene alkyl amines, polyoxyethylene alkyl amine oxides, fatty acid alkanol amides, alkylol amide, polyoxyethylene polyoxypropylene block polymer, or the like may be used.

Examples of the anionic surfactant include a higher fatty acid salt, a soap, an α-sulfo fatty acid methyl ester salt, a linear alkylbenzene sulfonate, an alkyl sulfate ester salt, an alkyl ether sulfate salt, a monoalkyl phosphate ester salt, α-olefin sulfonate, alkylbenzene sulfonate, alkyl naphthalene sulfonate, naphthalene sulfonate, alkane sulfonate, polyoxyethylene alkyl ether sulfate, sulfosuccinate, a polyoxyalkylene glycol alkyl ether phosphate ester salt, or the like.

Examples of the cationic surfactant include an alkyltrimethylammonium salt, a dialkyldimethylammonium salt, and an alkyldimethylbenzylammonium salts as quaternary ammonium series, N-methyl bishydroxyethylamine fatty acid ester hydrochloride as amine salts, or the like.

Examples of the amphoteric surfactant include an alkyl amino fatty acid salt as amino acids, an alkyl carboxyl betaine as betaines, and an alkyl amine oxide as amine oxides. The amphoteric surfactant is not limited thereto.

The content of the surfactant is preferably 0.1% to 2% by mass, and more preferably 0.1% to 2% by mass, and particularly preferably 0.2% to 1% by mass, with respect to the total mass (100% by mass) of the water-based ink composition.

1.5 Other Components

The water-based ink composition according to the present embodiment may contain a pH adjusting agent, a chelating agent, a preservative, a viscosity adjusting agent, a dissolution aid, an antioxidant, a fungicide, or the like in addition to the above-described components.

2. Method of Discharging Liquid Droplet (Ink Jet Recording Apparatus)

The method of discharging a liquid droplet according to the present embodiment includes discharging the above-described water-based ink composition onto a recording medium by a discharging head. The above-described water-based ink composition is excellent in the continuous printing stability even under the high temperature environment even when the water-based ink composition is applied to any ink jet recording apparatus.

In the ink jet recording apparatus including a new discharging head in which the side wall of the nozzle hole has a scallop structure, in a case where the new discharging head is placed under a high temperature environment, alignment deterioration easily occurs when a water-based ink containing the pigment is discharged. That is, a water-based ink in the passage cannot follow the movement of the meniscus, and the divided water-based ink is adhered on the uneven structure of the side wall of the passage. The alignment deterioration occurs due to thickening of the adhered water-based ink. Accordingly, it is considered that continuous printing stability is deteriorated. However, if in a case of the above-described water-based ink composition, it is excellent in the continuous printing stability in the high temperature environment even in a case of such an ink jet recording apparatus.

Next, an apparatus configuration of the ink jet recording apparatus which includes a new discharging head of which the side wall of the nozzle hole has a scallop structure which can preferably use the above-described water-based ink composition will be described.

Figure 1:
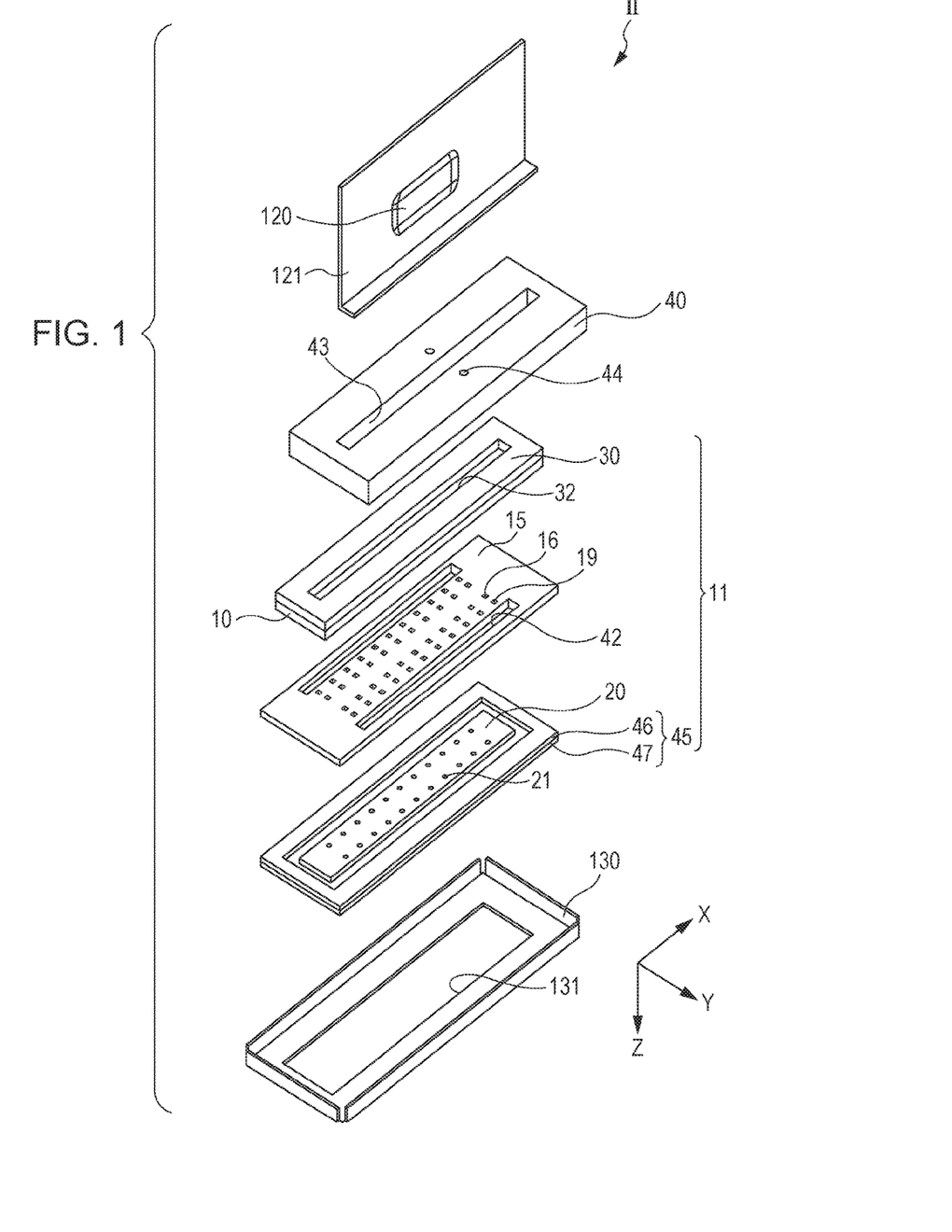
FIG. 1 is an exploded perspective view of an ink jet recording head that is an example of a discharging head of an ink jet recording apparatus.
Figure 2:
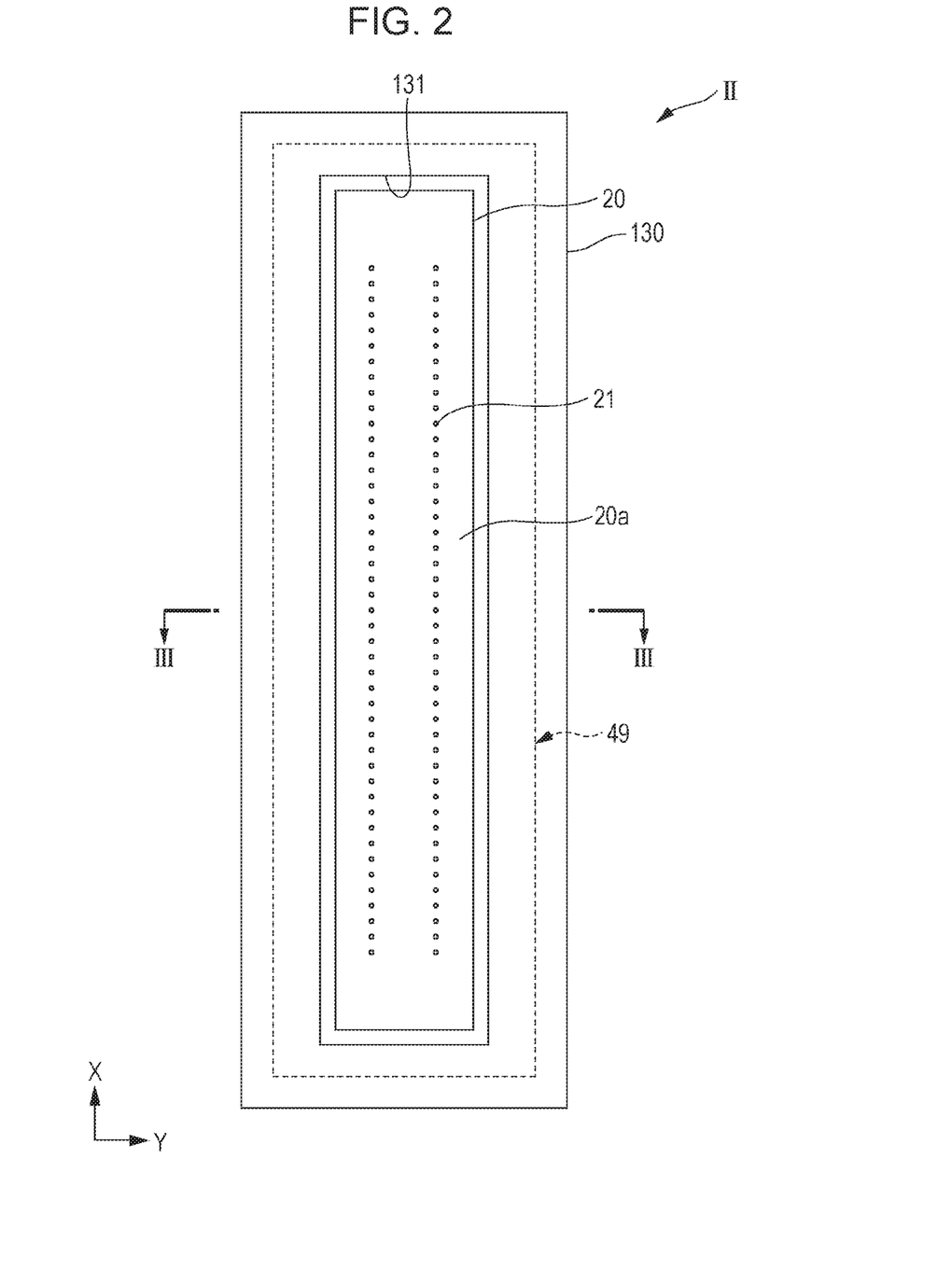
FIG. 2 is a plan view schematically illustrating the ink jet recording head.
Figure 3:
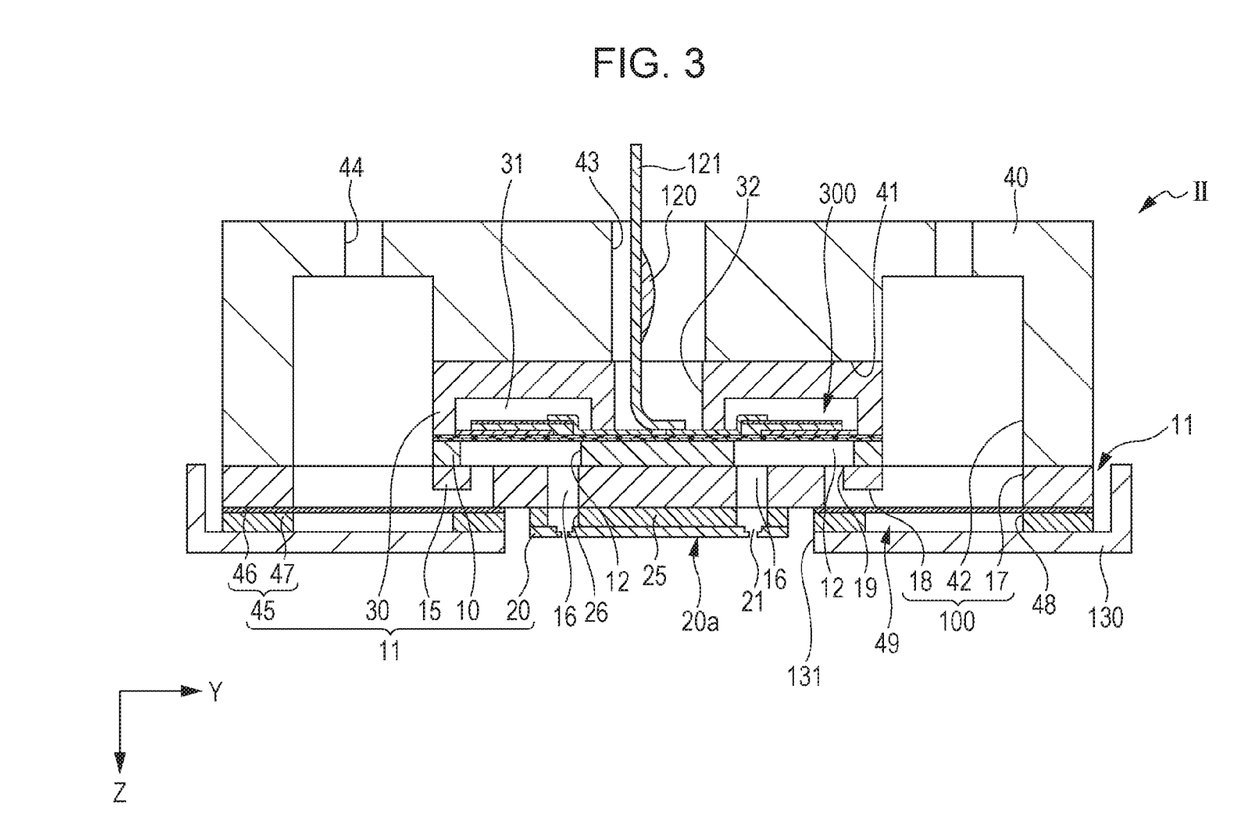
FIG. 3 is a sectional view of the ink jet recording head taken along the line III-III in FIG. 2.
Figure 4:
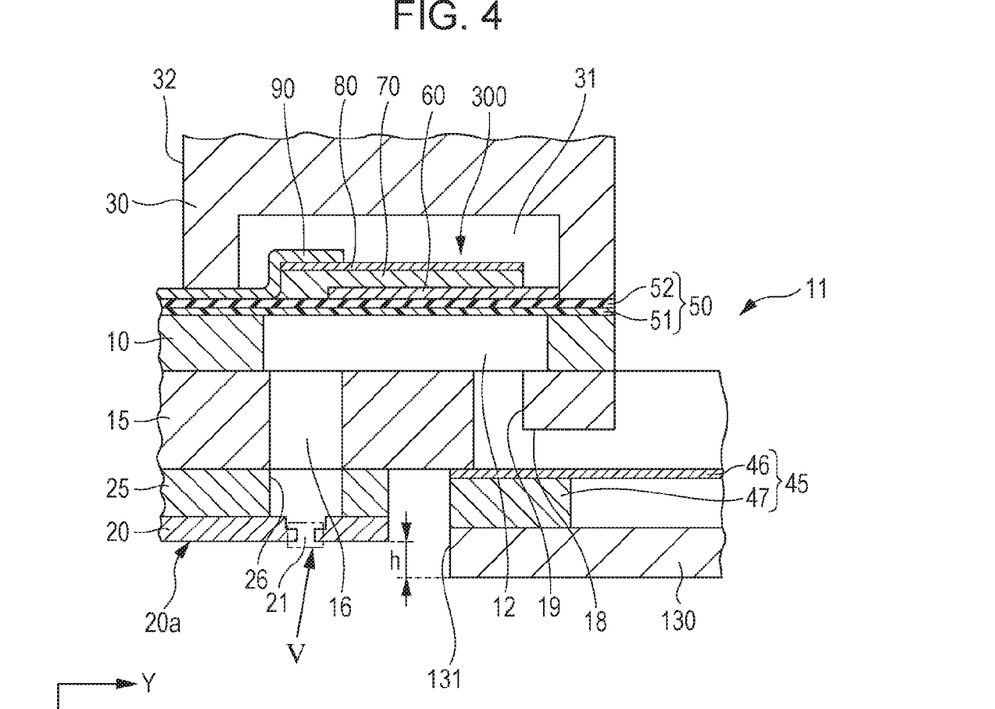
FIG. 4 is an enlarged sectional view of a main part of FIG. 3.
Figure 5:
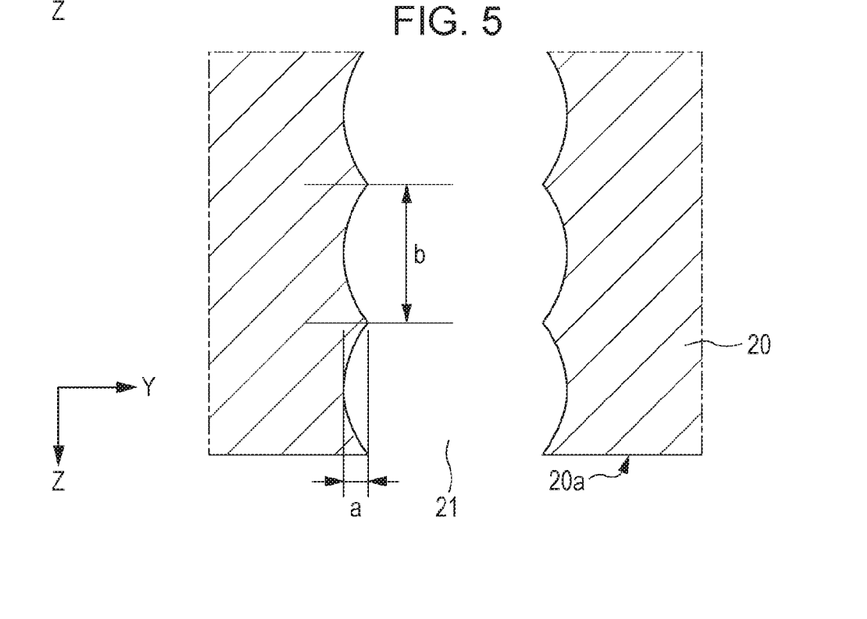
FIG. 5 is an enlarged sectional view of a region V in FIG. 4.
Figure 6:
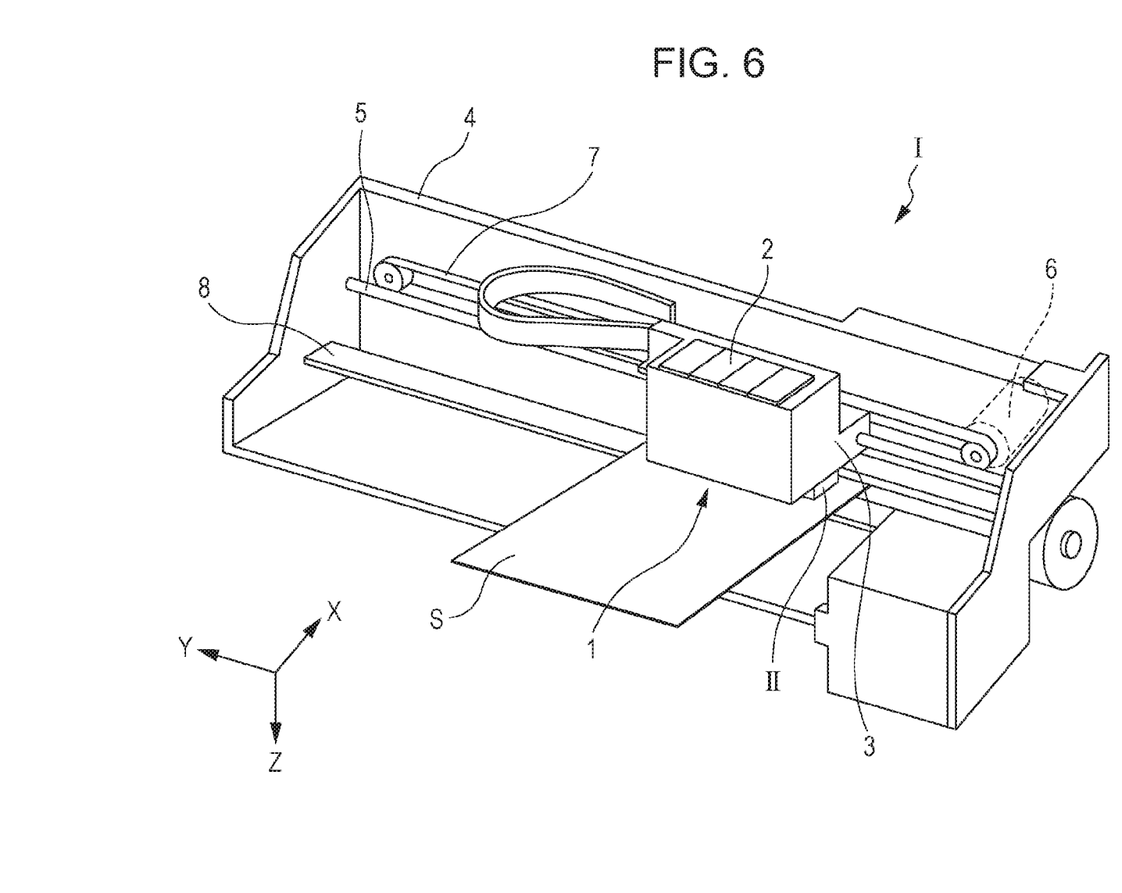
FIG. 6 is a schematic view schematically illustrating the ink jet recording apparatus.

FIG. 1 is an exploded perspective view of an ink jet recording head that is an example of a discharging head of an ink jet recording apparatus. FIG. 2 is a plan view schematically illustrating the ink jet recording head. FIG. 3 is a sectional view of the ink jet recording head taken along the line III-III in FIG. 2, and FIG. 4 is an enlarged sectional view of a main part of FIG. 3. FIG. 5 is an enlarged sectional view of a region V in FIG. 4, and is a sectional view illustrating a detailed shape of the vicinity of a nozzle opening. FIG. 6 is a schematic view schematically illustrating the ink jet recording apparatus.

As illustrated in drawings, an ink jet recording head II includes a plurality of members such as a head main body 11, a case member 40 which is fixed on one surface side of the head main body 11, and a cover head 130 which is fixed on the other surface side of the head main body 11. The head main body 11 is equipped with a passage forming substrate 10, a communication plate 15, a spacer 25, a nozzle plate 20, a protective substrate 30, and a compliance substrate 45.

As the passage forming substrate 10 which configures the head main body 11, a metal such as stainless steel or Ni, a ceramic material typified by $ZrO_2$ or $Al_2O_3$, a glass ceramic material, an oxide such as MgO or $LaAlO_3$, or the like can be used. The passage forming substrate 10 is formed of a silicon single crystal substrate. On the passage forming substrate 10, by anisotropic etching from the one surface side, pressure generating chambers 12 which are partitioned by a plurality of partition walls are arranged in parallel along a direction where a plurality of nozzle openings 21 for discharging the ink are arranged in parallel. Hereinafter, the direction will be referred to as a parallel arrangement direction of the pressure generating chamber 12 or a first direction X. In addition, on the passage forming substrate 10, a plurality of rows in which the pressure generating chambers 12 are arranged in parallel in the first direction X are provided, and in the present embodiment, two rows of pressure generating chamber 12 are provided. Hereinafter, the arrangement direction where plurality of rows of the pressure generating chambers 12 in which the pressure generating chamber 12 is formed is arranged in the first direction X will be referred to as a second direction Y.

In addition, in the passage forming substrate 10, a supply passage which has an opening area smaller than that of the pressure generating chamber 12 and imparts flow resistance of the ink flowing into the pressure generating chamber 12, or the like may be provided on one end portion side of the pressure generating chamber 12 in the second direction Y.

In addition, the communication plate 15, the spacer 25, and the nozzle plate 20 are sequentially stacked on the one surface side of the passage forming substrate 10. That is, the nozzle plate 20 including the communication plate 15 which is proved on one surface of the passage forming substrate 10, the spacer 25 which is provide at a surface side facing the passage forming substrate 10 of the communication plate 15, and the nozzle opening 21 which is provided at a surface side facing the communication plate 15 of the spacer 25 are provided.

A first nozzle communication passage 16 passing through the pressure generating chamber 12 and the nozzle opening 21 is provide on the communication plate 15. The communication plate 15 has an area greater than the passage forming substrate 10 and the nozzle plate 20 has an area smaller than the passage forming substrate 10. Since the nozzle opening 21 of the nozzle plate 20 is separated from the pressure generating chamber 12 by providing the communication plate 15 as described above, the ink in the pressure generating chamber 12 is less likely to be influenced by thickening due to evaporation of moisture in the ink caused by the ink in the vicinity of the nozzle opening 21. In addition, since the nozzle plate 20 is only required to cover the opening of the first nozzle communication passage 16 passing through the pressure generating chamber 12 and the nozzle opening 21, the area of the nozzle plate 20 can be relatively reduced, and the cost reduction can be achieved. The surface where the nozzle opening 21 of the nozzle plate 20 is open and the ink droplet is discharged is referred to as a liquid ejecting surface 20a.

In addition, a first manifold portion 17 and a second manifold portion 18 which configures a part of a manifold 100 are provided on the communication plate 15. The first manifold portion 17 is provided passing through the communication plate 15 in a thickness direction (a stacking direction of the communication plate 15 and the passage forming substrate 10).

In addition, the second manifold portion 18 is provided so as to open to the nozzle plate 20 side of the communication plate 15 without passing through the communication plate 15 in the thickness direction. Furthermore, on the communication plate 15, a supply communication passage 19 communicating with one end portion of the pressure generating chamber 12 in the second direction Y is independently provided for each pressure generating chamber 12. The supply communication passage 19 communicates with the second manifold portion 18 and the pressure generating chamber 12.

As such a communication plate 15, a metal such as stainless steel or Ni, a ceramic such as zirconium, or the like can be used. The communication plate 15 is preferably formed of a material having the same linear expansion coefficient as that of the passage forming substrate 10. That is, in a case where as the communication plate 15, the material having the greatly different linear expansion coefficient from that of the passage forming substrate 10, by heating or cooling the material, warpage occurs due to a difference in the linear expansion coefficient between the passage forming substrate 10 and the communication plate 15. By using the same material as the passage forming substrate 10, that is, a silicon single crystal substrate as the communication plate 15, it is possible to suppress the occurrence of the warpage due to heating, cracking due to heating, peeling, or the like in the substrate.

The spacer 25 has substantially the same area (area in the first direction X and the second direction Y) as the nozzle plate 20. Therefore, the spacer 25 is provided only at the position where the nozzle plate 20 is attached. That is, the spacer 25 is provided at the position where the compliance substrate 45 of the communication plate 15 is not attached. Therefore, as will be described in detail, the position where the nozzle plate 20 is attached, that is, the position of the surface of the spacer 25 where the nozzle plate 20 is attached is different from the position where the compliance substrate 45 is attached, that is, the position where the compliance substrate 45 is directly attached to the communication plate 15 in a discharging direction of the ink droplet, that is, a third direction Z that is the stacking direction of the communication plate 15 and the passage forming substrate 10.

A second nozzle communication passage 26 which communicates with the nozzle opening 21 by communicating with the first nozzle communication passage 16 is provided on the spacer 25. That is, the pressure generating chamber 12 communicates with the nozzle opening 21 through the first nozzle communication passage 16 of the communication plate and the second nozzle communication passage 26 of the spacer 25.

As the spacer 25, for example, a metal such as stainless steel or Ni, or a ceramic such as zirconium or silicon can be used. By using the same silicon single crystal substrate as the communication plate 15, as the spacer 25, it is possible to suppress the occurrence of the warpage, cracking, peeling, or the like due to heating or cooling in the substrate.

In addition, the spacer 25 may be selected such that a step h between the liquid ejecting surface 20a and the surface of the cover head 130 (a surface at the liquid ejecting surface 20a side) has a desired value based on the stacked thickness of the compliance substrate 45 and the cover head 130 that is a protection plate (total thickness in the third direction Z) and the thickness of the nozzle plate 20.

The pressure generating chambers 12 and the nozzle opening 21 passing through the first nozzle communication passage 16 and the second nozzle communication passage 26 are formed on the nozzle plate 20. That is, the nozzle openings 21 for discharging the same types of liquid (ink) are arranged in parallel in the first direction X, and two rows of the nozzle openings 21 which are arranged in parallel in the first direction X are formed in the second direction Y.

As such a nozzle plate 20, for example, a metal such as stainless steel (SUS), an organic material such as a polyimide resin, a silicon single crystal substrate, or the like can be used. By using the silicon single crystal substrate as the nozzle plate 20, it is possible to equalize the linear expansion coefficients of the nozzle plate 20 and the communication plate 15, and it is possible to suppress the occurrence of the warpage, cracking, peeling, or the like due to heating or cooling in the substrate.

On the other hand, a vibrating plate 50 is formed at a surface side facing the communication plate 15 of the passage forming substrate 10. As the vibrating plate 50, for example, an elastic film 51 formed of silicon oxide provided at the passage forming substrate 10 side and an insulating film 52 formed of zirconium oxide provided on the elastic film 51 can be provided. The liquid flow passage such as the pressure generating chamber 12 is formed by anisotropically etching the passage forming substrate 10 from one surface side (the surface side to which the nozzle plate 20 is bonded), and the other surface of the liquid flow passage such as the pressure generating chamber 12 is defined by the elastic film 51.

In addition, the protective substrate 30 having the substantially same size as that of the passage forming substrate 10 is bonded to the surface of a piezoelectric actuator 300 side of the passage forming substrate 10. The protective substrate 30 includes a holding portion 31 that is a space for protecting the piezoelectric actuator 300.

In addition, the case member 40 that defines the manifold 100 passing through the plurality of pressure generating chambers 12 and the head main body 11 is fixed to the head main body 11 having such a configuration. The case member 40 has substantially the same shape as that of the communication plate 15 described above in a plan view, and is bonded to the protective substrate 30 and also to the above-described communication plate 15. Specifically, the case member 40 has a concave portion 41 of a depth that accommodates the passage forming substrate 10 and the protective substrate 30 on the protective substrate 30 side. The concave portion 41 has an opening area wider than the surface bonded to the passage forming substrate 10 of the protective substrate 30. In a state where the passage forming substrate 10 and the like are accommodated in the concave portion 41, the opening surface of the concave portion 41 on the nozzle plate 20 side is sealed by the communication plate 15. Accordingly, a third manifold portion 42 is defined by the case member 40 and the head main body 11 on the outer peripheral portion of the passage forming substrate 10. The manifold 100 is configured by the first manifold portion 17 and the second manifold portion 18 provided on the communication plate 15 and the third manifold portion 42 defined by the case member 40 and the head main body 11.

As the material of the case member 40, for example, a resin, a metal, or the like can be used. By molding the resin material as the case member 40, production is possible at low cost.

The compliance substrate 45 is provided on the surface where the first manifold portion 17 and the second manifold portion 18 of the communication plate 15 are open. The compliance substrate 45 seals the opening at the liquid ejecting surface 20a side of the first manifold portion 17 and the second manifold portion 18.

That is, the compliance substrate 45 is directly fixed to the communication plate 15. Accordingly, the position of the surface of the spacer 25 to which the nozzle plate 20 is attached is different from the surface at the nozzle plate 20 side of the communication plate 15 to which the compliance substrate 45 is attached, in the third direction Z.

The matter that the position to which the nozzle plate 20 is attached and the position to which the compliance substrate 45 is attached are at the same position in the third direction Z means, for example, the nozzle plate 20 and the compliance substrate 45 are being attached on the same plane of the communication plate 15. The plane of the communication plate 15 includes a height variation due to a processing error when the surface of the communication plate 15 is processed into a planar shape. That is, by disposing the spacer 25 at the position where the nozzle plate 20 and the compliance substrate 45 are not fixed to the same surface as the communication plate 15 which is processed on the plane and the nozzle plate 20 of the communication plate 15 is fixed, the nozzle plate 20 is attached to the surface of the spacer 25, and the attachment positions of the nozzle plate 20 and the compliance substrate 45 in the third direction Z are different positions.

Such a compliance substrate 45 includes a sealing film 46 and a fixed substrate 47. The sealing film 46 is formed of a thin film having flexibility (for example, a thin film formed of polyphenylene sulfide (PPS), stainless steel (SUS), or the like and having a thickness of 20 μm or less) and the fixed substrate 47 is formed of a hard material such as a metal such as stainless steel (SUS). Since the region of the fixed substrate 47 facing the manifold 100 becomes an opening 48 completely removed in the thickness direction, one surface of the manifold 100 becomes a compliance portion 49 which is a flexible portion sealed only with the flexible sealing film 46.

An introduction path 44 for communicating with the manifold 100 and supplying the ink to each manifold 100 is provided on the case member 40. In addition, a connection port 43 which communicates with a through hole 32 of the protective substrate 30 and to which a wiring substrate 121 is inserted is provided on the case member 40.

The cover head 130 that is the protection plate is provided at the liquid ejecting surface 20a side of the head main body 11. The cover head 130 is bonded to the surface side of the compliance substrate 45 facing the communication plate 15, and the seals the space at a side of the compliance portion 49 facing the flow passage (manifold 100). An exposure opening 131 for exposing the nozzle opening 21 is provided on the cover head 130. The exposure opening 131 has an opening having a size to expose the nozzle plate 20, that is, the same opening as the compliance substrate 45.

In addition, the cover head 130 is provided such that an end portion is bent from the liquid ejecting surface 20a side so as to cover the side surface (a surface intersecting the liquid ejecting surface 20a) of the head main body 11.

In the ink jet recording head II having such a configuration, when the ink is ejected, a voltage is applied to each piezoelectric actuator 300 corresponding to the pressure generating chamber 12 in accordance with a signal from a driving circuit 120. Accordingly, the vibrating plate 50 together with the piezoelectric actuator 300 is bent and deformed. Therefore, the pressure in the pressure generating chamber 12 increases and the ink droplet is discharged from the nozzle opening 21. In the ink jet recording head II, a passage from the connection portion 43 to the nozzle opening 21 is referred to as the liquid passage. That is, the liquid passage is configured of the connection portion 43, the manifold 100, the supply communication passage 19, the pressure generating chamber 12, the first nozzle communication passage 16, the second nozzle communication passage 26, and the nozzle opening 21.

The ink jet recording head II having such a configuration includes a first liquid passage (pressure generating chamber 12) including the vibrating plate 50 extending in a planar direction (Y direction) and a plurality of second liquid passages (supply communication passage 19, second nozzle communication passage 26, and first nozzle communication passage 16) connecting to the first liquid passage in a vertical direction (Z direction). Since in the ink jet recording head II, the distance between the liquid passages is longer and the volume of the liquid passage is greater than that of the conventional ink jet recording head, the drying of the ink in the vicinity of the nozzle can be reduced. Therefore, since it is possible to reduce the thickening of the ink at the nozzles which do not eject the ink, the discharging stability of the ink is improved.

On the other hand, as illustrated in FIG. 5, in a case where a shape of the side wall in the vicinity of the nozzle opening 21 has the scallop structure, the water-based ink in the vicinity of the nozzle opening 21 cannot follow the movement of the meniscus when the ink is discharged, and the water-based ink is remained in the uneven structure of the side wall in the vicinity of the nozzle opening 21. The remained water-based ink thickens under the high temperature environment. Accordingly, discharging defects (discharging bending, scattering the discharging, or the like) occurs, and the continuous printing stability tends to be impaired. However, according to the above-described water-based ink composition, it is possible to follow the movement of the meniscus by lowering the viscosity in the low shearing region and the viscosity in the high shearing region. Accordingly, it is possible to reduce the possibility that the ink remains on the uneven structure of the side wall in the vicinity of the nozzle opening 21. Therefore, the continuous printing stability under the high temperature environment is improved. The side wall in the vicinity of the nozzle opening 21 is a side wall in a region within about 100 μm from the nozzle opening 21.

In addition, as illustrated in FIG. 5, when a depth of a concave portion formed on the side wall surface in the vicinity of the nozzle opening 21 is defined as a and a distance between adjacent convex portions is defined as b, the ratio b/a is preferably b/a≥4, and more preferably b/a≥5, and particularly preferably b/a≥15. When the value of b/a is in the above-described range, it is possible to further reduce the possibility that the ink remains in the uneven structure of the side wall of the second liquid passage at the scallop step portion of the water-based ink composition. Therefore, the continuous printing stability in the high temperature environment is further improved.

Here, the depth a of the concave portion and the distance b between the adjacent convex portions are 1 μm or less, respectively. The depth a of the concave portion is preferably 0.01 μm to 0.3 μm, more preferably 0.015 μm to 0.2 μm, and particularly preferably 0.02 μm to 0.15 μm. On the other hand, the distance b between the adjacent convex portions is preferably 0.3 μm to 1 μm, more preferably 0.4 μm to 0.8 μm, and particularly preferably 0.45 μm to 0.7 μm.

The ink jet recording head II configures a part of an ink jet recording head unit including the ink passage communicating with the ink cartridge or the like and is mounted on the ink jet recording apparatus. FIG. 6 is a schematic view illustrating schematically illustrating an example of the ink jet recording apparatus.

In an ink jet recording apparatus I illustrated in FIG. 6, in an ink jet recording head unit 1 (hereinafter, also referred to as the head unit 1) including a plurality of ink jet recording heads II, a cartridge 2 configuring the ink supply unit is detachably provided, and a carriage 3 on which the head unit 1 is mounted is detachably provided on the carriage axis 5 which is attached to an apparatus main body 4 in the axis direction. For example, the recording head units 1 discharge a black ink composition and a color ink composition, respectively.

The driving force of a driving motor 6 is transmitted to the carriage 3 through a plurality of gears (not shown) and a timing belt 7. Accordingly, the carriage on which the head unit 1 is mounted is moved along the carriage axis 5. On the other hand, a platen 8 is provided on the apparatus main body 4 along the carriage axis 5, and a recording sheet S that is a recording medium such as a paper fed by a paper feed roller (not shown) is wrapped around the platen 8 and is transported.

In the above-described ink jet recording apparatus I, the ink jet recording head II (head unit 1) is mounted on the carriage 3 and moves in the main scanning direction. However, it is not particularly limited thereto. For example, the invention can also be applied to a so-called line type recording apparatus in which the ink jet recording head II is fixed and printing is performed by simply moving the recording sheet S such as paper in the sub scanning direction.

In addition, in the above-described example, the ink jet recording apparatus I is configured such that an ink cartridge 2 that is liquid storage unit is mounted on the carriage 3. However, it is not limited thereto, and for example, the storage unit may be connected with the ink jet recording head II via a supply pipe such as a tube by fixing the liquid storage unit such as an ink tank to the apparatus main body 4. In addition, the liquid storage unit may not be mounted on the ink jet recording apparatus.

Furthermore, the invention is widely applied to all kinds of liquid ejecting heads. For example, the invention can also be applied to a recording head such as various types of ink jet recording heads to be used in an image recording apparatus such as printer, a color material ejecting head used for manufacturing a color filter such as a liquid crystal display, an electrode material ejecting head used for forming an electrode of an organic EL display, a FED (field emission display), a bioorganic material ejecting head used for manufacturing biochips, or the like.

3. Examples

Hereinafter, the invention will further be described in detail based on examples. However, the invention is not limited to the examples. Unless otherwise specified, "parts" and "%" in the examples and comparative examples are a mass basis.

3.1 Preparation of Water-Based Ink Composition

The pigment and the ammonium salt of the styrene-acrylic acid copolymer (Trade name "Joncryl 63", manufactured by BASF, weight average molecular weight=12,500, 30% of polymer component: Dispersant) were dispersed together with glass beads (Diameter=1.7 mm, 1.5-fold of the amount of mixture) in a sand mill (manufactured by Yasukawa Seisakusho Co., Ltd.) for 2 to 5 hours. By properly adjusting the dispersion time in 2 to 5 hours, the average particle diameter of the pigment was set to the values illustrated in Table 2 below. Next, the glass beads where removed, the other components were added, the mixture was stirred at a room temperature for 30 minutes. The mixture was filtered with a 5 μm pore size membrane filter to obtain the water-based ink compositions shown in Table 2 below.

3.2 Evaluation of Physical Properties of Water-Based Ink Composition

Physical properties of the water-based ink composition obtained above were evaluated in the following manner.

Particle Size Distribution Measurement

A sample was obtained by diluting the pigment with the pure water such that the pigment concentration in the obtained water-based ink composition becomes 50 ppm. By measuring the sample with the dynamic light scattering type nano-track particle size analyzer (manufactured by Nikkiso Co., Ltd., Type "Nanotrac 150"), the average particle diameter D50 of the pigment contained in each water-based ink composition was obtained.

Viscosity and Yield Value

The viscosity of the obtained water-based ink composition at 20° C. was obtained by the Rheometer MCR301 (manufactured by Anton Paar). Furthermore, the obtained water-based ink composition and the water-based ink composition obtained by evaporating the water by 25% were subjected to the rheology measurement with the Rheometer MCR301 (manufactured by Anton Paar). The yield values of inks were obtained by analyzing the obtained data by Casson-Plot.

Temperature: 20° C.

Shearing rate: 0.01 to 1.00 (1/s)

3.3 Preparing Ink Jet Recording Apparatus

The ink jet recording apparatus including the discharging head illustrated in FIGS. 1 to 5 described above was prepared. The discharging head of the ink jet recording apparatus is referred to as a "head A". In FIG. 5, when a depth (step) of the concave portion which is formed on the side wall surface of the liquid passage is defined as a, and a distance (pitch) between adjacent convex portions is defined as b, the level of each head A was set to three levels as shown in Table 1 below.

TABLE 1

| | Head | | |
|---|---|---|---|
| Level | a: step (μm) | b: pitch (μm) | b/a |
| A-1 | 0.12 | 0.52 | 4.3 |
| A-2 | 0.04 | 0.55 | 13.8 |
| A-3 | 0.02 | 0.58 | 29.0 |

3.4 Evaluation Method (Continuous Printing Evaluation)

The evaluation was carried out by the following test using each water-based ink composition prepared above. Firstly, a cartridge dedicating for the prepared ink jet recording apparatus (manufactured by Seiko Epson Corporation, Modified product of Type "SC-T7050") including the head A is filled with the prepared water-based ink composition. Next, the printing environment was changed to 40° C. and 20% of R.H., and a nozzle check pattern was printed using the ink jet recording apparatus. Thereafter, in a state where the printing environment was maintained in 40° C. and 20% of R.H., a natural image was printed on a photographic paper "Glossy" PXMC44R13 (manufactured by Seiko Epson Corporation) for 2 hours, and then landing position misalignments of the initial ink and the ink after printing were measured. The measurement of the degree of the misalignment was performed by setting an initial dot with the Smart Scope ZIP250 (manufactured by OGP Inc.) to 0, measuring the position of each dot, and calculating the degree of the misalignment of the dot positions before and after continuous printing in the Y-axis direction (media feeding direction). The distance between the media and the head A is 1.2 mm (platen gap). Evaluation criteria are as follows.

Evaluation Criteria

A: Number of dots with the landing position misalignment of 50 μm or more is 1 dot or less.

B: Number of dots with the landing position misalignment of 50 μm or more is 5 dots or less.

C: Number of dots with the landing position misalignment of 50 μm or more is more than 5 dots more than 1 dot.

Sedimentation Evaluation

The water-based ink composition was added that the total weight of the centrifuge tube, the lid, and water-based ink composition was 55 g. The centrifuge tube with the lid was set in a centrifuge (manufactured by Hitachi Koki Co., Ltd., Trade name "CR-20B2", ROTOR NO. 36), treated at 10,000 rpm for 15 minutes, and collected the so-called mass ink (the ink in region of 5 cm or less from the gas-liquid interface) ink to measure the absorbance. The measurement of the absorbance was carried out such that the mass ink was diluted 1000-fold with pure water, the absorption spectrum was measured with a UV visible spectrophotometer (manufactured by Hitachi, Ltd., Trade name "U-3300"), and the absorbance of the top peak of 111±5 nm. The ratio of the absorbance of the ink before centrifugal separation and the absorbance of the mass ink after centrifugal separation was calculated and evaluated according to the following criteria.

Evaluation Criteria

A: the mass concentration is 50% or more of the initial concentration.

B: the mass concentration is 35% or more and less than 50% of the initial concentration.

C: the mass concentration is less than 35% of the initial concentration.

3.5 Evaluation Result

The compositions and the evaluation results of the water-based ink composition of examples and comparative examples is shown in Table 2 below. In Table 2 below, the numerical value of each component represents the mass %.

TABLE 2

| | Material | Example 1 | Example 2 | Example 3 | Example 4 | Example 5 | Example 6 | Example 7 |
|---|---|---|---|---|---|---|---|---|
| Pigment | PR202/PV19 Solid solution | 5.0 | 5.0 | 5.0 | 5.0 | 5.0 | 5.0 | |
| | PR202 | | | | | | | |
| | PR122 | | | | | | | 5.0 |
| Dispersant | Styrene-acrylic acid copolymer ammonium salt (solid) | 3.5 | 3.5 | 3.5 | 3.5 | 3.5 | 3.5 | 3.5 |
| Water-soluble organic solvent | Glycerin | 15.0 | 15.0 | 15.0 | 15.0 | 15.0 | 15.0 | 15.0 |
| | Triethylene glycol | 4.5 | 4.5 | 4.5 | 4.5 | 4.5 | 4.5 | 4.5 |
| | 1,2-hexanediol | 3.0 | 3.0 | 3.0 | 3.0 | 3.0 | 3.0 | 3.0 |
| | Triethylene glycol monobutyl ether | 1.0 | 1.0 | 1.0 | 1.0 | 1.0 | 1.0 | 1.0 |
| Preservative | Triethanolamine | 1.0 | 1.0 | 1.0 | 1.0 | 1.0 | 1.0 | 1.0 |
| Surfactant | SAG503A | 0.9 | 0.9 | 0.9 | 0.9 | 0.9 | 0.9 | 0.9 |
| | Pure water | 66.1 | 66.1 | 66.1 | 66.1 | 66.1 | 66.1 | 66.1 |
| | Total | 100.0 | 100.0 | 100.0 | 100.0 | 100.0 | 100.0 | 100.0 |
| Average particle diameter | D50(nm) | 80 | 80 | 80 | 100 | 130 | 160 | 100 |
| Ink viscosity | (mPa·s) | 4.5 | 4.5 | 4.5 | 4.2 | 4.2 | 4.0 | 4.0 |
| Yield value | Ink (mPa) | 0.0 | 0.0 | 0.0 | 0.0 | 0.0 | 0.0 | 0.0 |
| | Water 25% evaporated ink | 0.6 | 0.6 | 0.6 | 0.2 | 0.0 | 0.0 | 0.0 |
| Continuous printing evaluation | Types of head A | A-2 | A-1 | A-3 | A-2 | A-2 | A-2 | A-2 |
| | Landing position misalignment | B | B | B | A | A | A | A |
| | Sedimentation evaluation | A | A | A | A | A | B | A |

TABLE 2-continued

| | Material | Example 8 | Example 9 | Comparative Example 1 | Comparative Example 2 | Comparative Example 3 |
|---|---|---|---|---|---|---|
| Pigment | PR202/PV19 Solid solution PR202 | | 5.0 | 5.0 | 5.0 | 5.0 |
| | PR122 | 5.0 | | | | |
| Dispersant | Styrene-acrylic acid copolymer ammonium salt (solid) | 3.5 | 3.5 | 3.5 | 3.5 | 3.5 |
| Water-soluble organic solvent | Glycerin | 15.0 | 15.0 | 15.0 | | 45.0 |
| | Triethylene glycol | 4.5 | 4.5 | 4.5 | 4.5 | 4.5 |
| | 1,2-hexanediol | 3.0 | 3.0 | 3.0 | 3.0 | 3.0 |
| | Triethylene glycol monobutyl ether | 1.0 | 1.0 | 1.0 | 1.0 | 1.0 |
| Preservative | Triethanolamine | 1.0 | 1.0 | 1.0 | 1.0 | 1.0 |
| Surfactant | SAG503A | 0.9 | 0.9 | 0.9 | 0.9 | 0.9 |
| | Pure water | 66.1 | 66.1 | 66.1 | 81.1 | 36.1 |
| | Total | 100.0 | 100.0 | 100.0 | 100.0 | 100.0 |
| Average particle diameter | D50(nm) | 100 | 170 | 70 | 100 | 100 |
| Ink viscosity | (mPa · s) | 4.0 | 4.0 | 4.6 | 1.8 | 8.5 |
| Yield value | Ink (mPa) | 0.0 | 0.0 | 0.2 | 0.0 | 0.0 |
| | Water 25% evaporated ink | 0.0 | 0.0 | 0.8 | 0.0 | 0.0 |
| Continuous printing evaluation | Types of head A | A-2 | A-2 | A-2 | A-2 | A-2 |
| | Landing position misalignment | A | A | C | C | C |
| | Sedimentation evaluation | A | C | A | B | A |

In Table 2 above, Abbreviations of the components are as follows.

PR: C.I. Pigment Red
PV: C.I. Pigment Violet
Styrene-acrylic acid copolymer ammonium salt: manufactured by BASF, Trade name "Joncryl 63", weight average molecular weight=12,500, 30% of Resin Aqueous Solution
SAG503A: manufactured by Nissin Chemical Co., Ltd., Trade name "Silface SAG503A", Silicone Surfactant From the results of Table 2, according to the water-based ink composition according to the invention, it is clear that by reducing the difference between the viscosity the low shearing region and the viscosity of the high shearing region, the continuous printing stability is improved even under the high temperature environment. In addition, it is clear that specifically, the water-based ink composition according to the invention has a good continuous printing stability under the high temperature environment in the head of which the nozzle has the scallop structure.

The invention is not intended to be limited to the embodiments described above, and various new alterations are possible. For example, the invention includes constitutions that are substantially identical with the constitutions described in the embodiments (for example, constitutions having identical functions, methods and results, or constitutions having identical purposes and results). Furthermore, the invention includes constitutions in which the parts that are not essential in the constitutions described in the embodiments have been changed. Further, the invention includes constitutions which provide the same operating effects, or constitutions which can achieve the same purpose, as the constitutions described in the embodiments. Further, the invention includes constitutions to which known technologies have been added to the constitutions described in the embodiments.

The entire disclosure of Japanese Patent Application No. 2016-127759, filed Jun. 28, 2016 is expressly incorporated by reference herein.

What is claimed is:

1. A water-based ink composition comprising:
a pigment, wherein an average particle diameter of the pigment is 80 nm or more and less than 160 nm;
water; and
a dispersant,
wherein a viscosity at 20° C. is in a range of 2 mPa·s to 7 mPa·s, and
wherein a yield value at 20° C. is less than 0.2 mPa, and the yield value at 20° C. when evaporating 25% of the water is less than 0.8 mPa,
wherein the pigment has a quinacridone skeleton, and
wherein the dispersant is water soluble.

2. The water-based ink composition according to claim 1, wherein the pigment having the quinacridone skeleton is at least one selected from the group consisting of C.I. Pigment Red 122, C.I. Pigment Red 202, and C.I. Pigment Violet 19.

3. The water-based ink composition according to claim 1, wherein the water-based ink composition is for use in an ink jet recording apparatus including a discharging head having a nozzle substrate in which a discharging port for discharging a liquid is formed and a side wall surface of the discharging port has a plurality of scallop-shaped portions.

4. The water-based ink composition according to claim 3, wherein when a depth of a concave portion formed on the side wall surface in the vicinity of the discharging port is defined as a and a distance between adjacent convex portions is defined as b, a relation of b/a≥4 is satisfied.

5. A method of discharging a liquid droplet comprising:
discharging the water-based ink composition according to claim 1 onto a recording medium by a discharging head.

6. A method of discharging a liquid droplet comprising:
discharging the water-based ink composition according to claim 1 onto a recording medium by a discharging head.

7. A method of discharging a liquid droplet comprising:
discharging the water-based ink composition according to claim 2 onto a recording medium by a discharging head.

8. The method of discharging a liquid droplet according to claim 5,
wherein the discharging head includes a nozzle substrate in which a discharging port for discharging a liquid is formed, and has a plurality of scallop-shaped portions formed on a side wall surface in the vicinity of the discharging port.

9. The method of discharging a liquid droplet according to claim 6,
wherein the discharging head includes a nozzle substrate in which a discharging port for discharging a liquid is formed, and has a plurality of scallop-shaped portions formed on a side wall surface in the vicinity of the discharging port.

10. The method of discharging a liquid droplet according to claim 7,
wherein the discharging head includes a nozzle substrate in which a discharging port for discharging a liquid is formed, and has a plurality of scallop-shaped portions formed on a side wall surface in the vicinity of the discharging port.

11. The method of discharging a liquid droplet according to claim 8,
wherein when a depth of a concave portion formed on the side wall surface in the vicinity of the discharging port is defined as a, and a distance between adjacent convex portions is defined as b, a relation of $b/a \geq 4$ is satisfied.

12. The method of discharging a liquid droplet according to claim 9,
wherein when a depth of a concave portion formed in the side wall in the vicinity of the discharging port is defined as a, and a distance between adjacent convex portions is defined as b, a relation of $b/a \geq 4$ is satisfied.

13. The method of discharging a liquid droplet according to claim 10,
wherein when a depth of a concave portion formed in the side wall in the vicinity of the discharging port is defined as a, and a distance between adjacent convex portions is defined as b, a relation of $b/a \geq 4$ is satisfied.

14. The water based ink composition according to claim 1,
wherein the average particle diameter of the pigment is an average particle diameter without the dispersant.

* * * * *